United States Patent [19]

Siczek et al.

[11] Patent Number: 5,067,145
[45] Date of Patent: Nov. 19, 1991

[54] MOBILE X-RAY APPARATUS

[76] Inventors: Bernard W. Siczek; Aldona A. Siczek, both of 1252 Chinook Way, Boulder, Colo. 80303

[21] Appl. No.: 494,478
[22] Filed: Mar. 16, 1990
[51] Int. Cl.$^5$ .............................................. H05G 1/02
[52] U.S. Cl. .................................... 378/198; 378/210
[58] Field of Search .......................................... 378/198

[56] References Cited

U.S. PATENT DOCUMENTS 3,790,805 2/1974 Foderaro ............................. 378/198
4,989,229 1/1991 Negrelli et al. ..................... 378/198

FOREIGN PATENT DOCUMENTS 2404989 9/1978 France ................................ 378/198

Primary Examiner—Craig E. Church

[57] ABSTRACT

A mobile X-ray apparatus for use in X-ray in diagnostic examinations comprising a base on wheels having an arm structure mounted thereon for supporting an X-ray tube, wherein this arm structure comprises a first structure of telescopic construction utilizing a pulley principle for an extended vertical travel of the X-ray tube and yet compactness, and further including a constant spring mechanism for allowing manual positioning, a second structure moveably mounted on the first structure for both horizontal and vertical displacement of the X-ray tube which structure includes a parallelogram and a horizontal telescopic member, a steering assist mechanism including motors providing power to each wheel of one pair of the wheels and being independently energized so that a power differential can be created as desired to assist in turning the apparatus. This disclosure further includes a brake mechanism for effective control of positioning of any moveable structure of an X-ray apparatus.

1 Claim, 2 Drawing Sheets

MOBILE X-RAY APPARATUS

FIELD OF INVENTION

This invention relates to a mobile X-ray apparatus for use in diagnostic examinations and medical treatments.

BACKGROUND OF INVENTION

The use of mobile X-ray apparatus for diagnostic examinations is well known. However, improvements in such X-ray mobile apparatus is deemed to be useful. In particular, now known mobile apparatus has an X-ray tube supported by an elongated, non-retractable vertical arm which obstructs vision when the apparatus is being moved and makes it more difficult to go through a door or to transport and more, is difficult to steer.

SUMMARY OF INVENTION

This invention provides an improved mobile X-ray apparatus for use in an X-ray diagnostic examinations comprising a novel support structure for an X-ray tube, a novel steering assist mechanism and a novel brake mechanism.

The support structure for the X-ray tube according to this invention comprises: a vertically extending structure of telescopic construction including three members in a relative sliding relationship therebetween in a vertical direction, wherein a first of these three members is affixed to the base, a second member supported by a constant force spring mechanism, this second member having a pulley mounted thereon with a cable routed over the pulley and having its respective ends fasten to the first and a third member so that a vertical displacement of the second member results in a twice as long vertical displacement of the third member, a parallelogram moveably mounted on this third member and having a horizontally extending telescopic member mounted thereon for both vertical and horizontal positioning of the X-ray tube.

The telescopic construction of the vertically extending structure allows for retracting this structure so that visibility is not obstructed while the apparatus is being moved or transported and more, makes the apparatus more compact for easier passage through a door, all these without compromising the range of the vertical movement of the X-ray tube. Utilization of the pulley principle allows for an extended vertical displacement and compactness. The parallelogram and the horizontally extending telescopic member additionally improves positioning of the X-ray tube. The constant force spring mechanism serves as a counter balance for the X-ray tube allowing for manual positioning.

The steering assist mechanism includes two motors with worm reducers for providing power to one pair of wheels supporting the apparatus and being independently energized as controlled by a strain sensor so that a power differential can be created to assist in turning the apparatus as desired for improved maneuverability.

The brake mechanism according to this invention allows for effective control of positioning of any moveable structure of the apparatus in any desired position; each moveable structure having its own braking mechanism. All the brake mechanisms can be released simultaneously by an electromagnetic action or individually by manual action.

BRIEF DESCRIPTION OF THE FIGURES

The present invention may be described with a greater clarity by referring to the following figures.

DESCRIPTION OF THE ILLUSTRATED EMBODIMENT

The accompanying drawings illustrate a presently preferred embodiment of the invention according to the mode so far devised for the practical application of the principles thereof.

Figure 1:
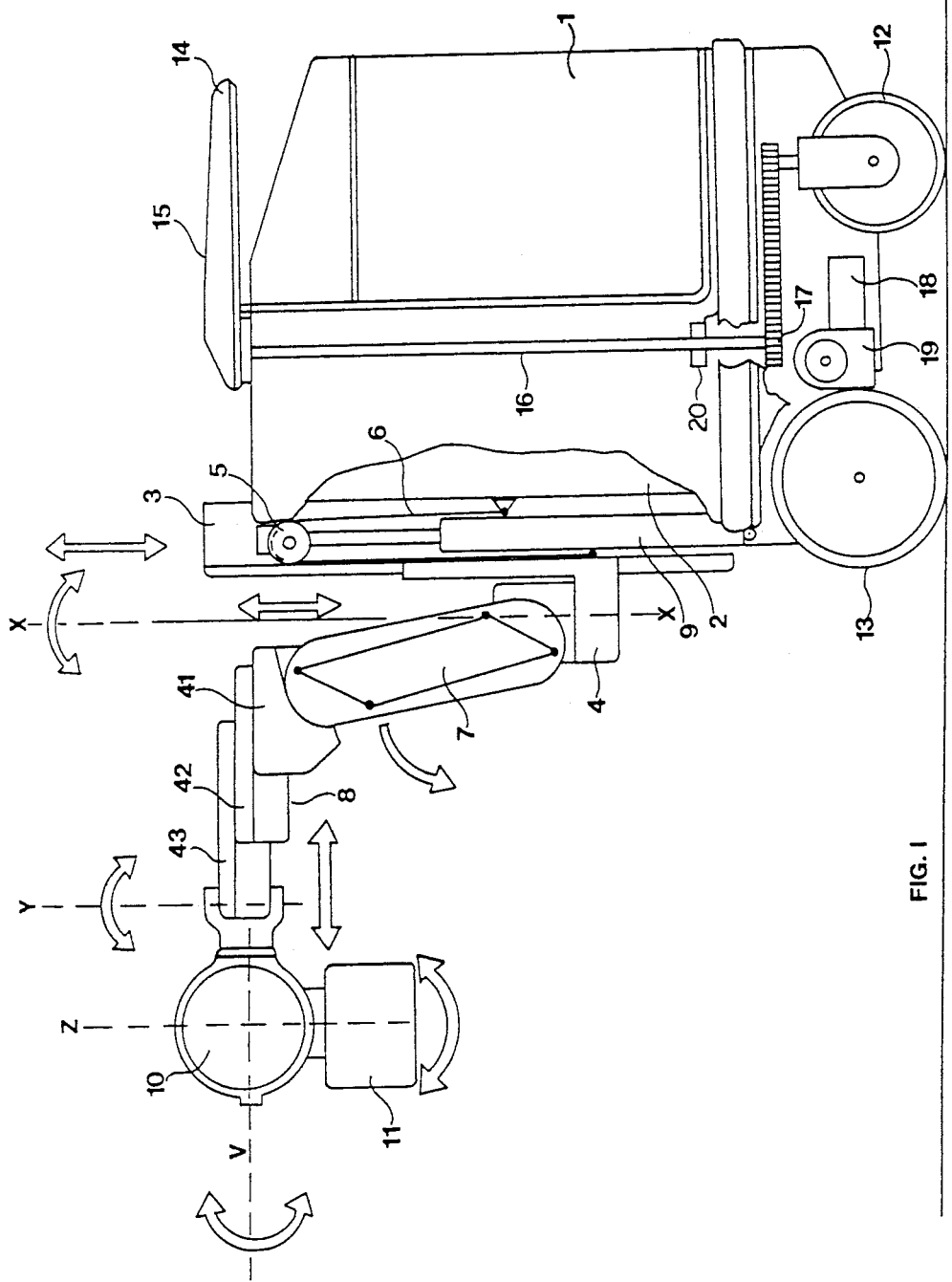
FIG. 1 of a mobile X-ray apparatus.

FIG. 1 is a side view of a X-ray mobile apparatus constructed in accordance with the present invention. This mobile X-ray apparatus comprises a base 1 supported on two pairs of wheels 12 and 13. Base 1 includes a vertically extending structure of telescopic construction comprising three members, a first member 2 is attached to base 1 and has a second member 3 mounted thereon in a sliding engagement, which second member has a third member 4 mounted thereon for a relative sliding movement therebetween. Second member 3 is supported by a constant force spring mechanism (such as an air spring) 9 affixed to base 1. A pulley 5 is mounted on second member 3 and has a cord 6 routed thereover and having its respective ends fasten to first member 2 and to third member 4 so that a vertical displacement of second member 3 results in a twice as long vertical displacement of the third member 4.

A parallelogram structure 7 is rotateably mounted on third member 4 and has horizontally extending mounted thereon for supporting an X-ray tube 10 with a collimator 11. Horizontally extending structure 8 includes three members 41, 42, 43 in a relative sliding arrangement therebetween for a displacement of the X-ray tube in a horizontal direction. Constant force spring mechanism 9 counterbalances all of the vertically moveable parts.

Wheels 12 are freely rotateable and controlled by handles 14 disposed on a control panel 15 (which panel includes controls for generating X-ray radiation). Rotational force applied to handles 14 is transmitted to wheels 12 by means of a vertical shaft 16 connected to a transmission means 17.

A steering assist mechanism includes two motors 18 with gear worm reducers 19 for providing power to wheels 13, which motors are independently energized as controlled by a strain sensor 20 coupled to vertical shaft 16, so that rotation of the shaft changes a parameter of the strain sensor such as electrical resistance and dependently on the value of the parameter a power differential is created to assist in turning the apparatus as desired.

Figure 2:
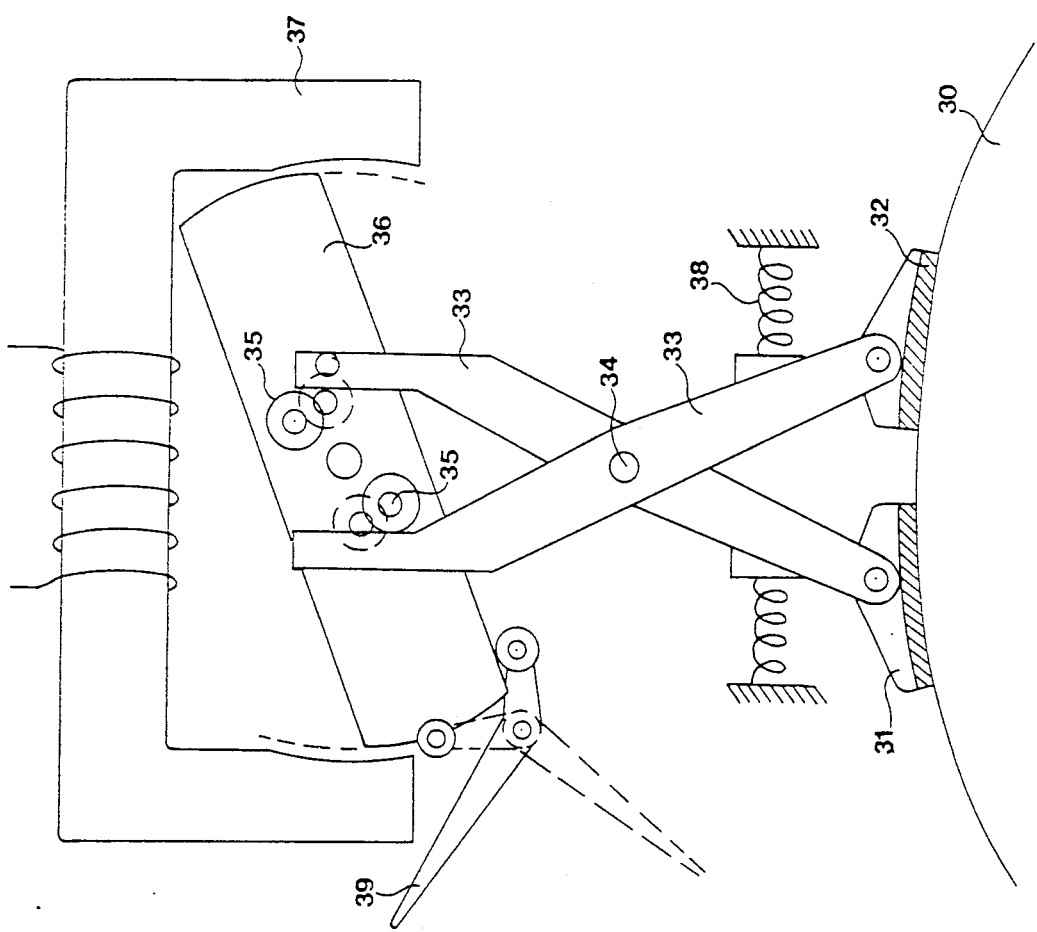
FIG. 2 is a schematic drawing of a brake mechanism.

FIG. 2 illustrates a braking mechanism applied to a moveable surface 30 which surface can be other than flat. This braking mechanism comprises: arms 33 pivotally secured at point 34 and each having at one end a block 31 with a brake shoe 32 attached thereto, which brake shoes are applied to surface 30, springs 38 exerting pressure on arms 33 and providing braking force, a beam 36 with rollers 35 disposed intermediate two poles of an electromagnet 37 in a pivoting relationship so that when electromagnet 37 is energized beam 36 pivots causing brake shoes 32 to separate from surface 30 counter to the action of springs 38. This separation can also be accomplished manually by using a handle 39 to pivot beam 36.

Angulation between arms 33 and surface 30 is selected so that when surface 30 is being moved in one direction, one of the brake shoes exerts additional braking action and when surface 30 is being moved in an opposite direction the other shoe does it.

The X-ray tube can also be rotateable about axes X, Y, Z, V. A number of the braking mechanisms can be used to hold the X-ray tube in any desired position. These mechanism can be all simultaneously released by electromagnetic action or individually by manual action.

What is claimed is:

1. A mobile X-ray apparatus for use in medical diagnostic examinations comprising:
 a base comprising:
  an X-ray generator,
  a steering means,
  a sensing means,
 wheels supporting said bas and including at least one manually steerable wheel and one pair of wheels wherein each wheel is connected to a power means, and wherein:
  said steering means are connected to the manually steerable wheel or wheels,
  said sensing means are coupled to said steering means for sensing steering momentum and providing differential energizing of the power means for differentially driving said second pair of the wheels.

* * * * *